(12) United States Patent
Hayashi et al.

(10) Patent No.: US 6,359,284 B1
(45) Date of Patent: Mar. 19, 2002

(54) SCANNER TYPE FLUORESCENCE DETECTION APPARATUS

(75) Inventors: Toshinori Hayashi; Takahiko Ishiguro, both of Kanagawa (JP)

(73) Assignee: Tosoh Corporation, Yamaguchi-Ken (JP)

( * ) Notice: Subject to any disclaimer, the term of this patent is extended or adjusted under 35 U.S.C. 154(b) by 0 days.

(21) Appl. No.: 09/391,161

(22) Filed: Sep. 8, 1999

(30) Foreign Application Priority Data

Sep. 9, 1998 (JP) .......................................... 10-254913

(51) Int. Cl.⁷ .............................................. G01N 35/04
(52) U.S. Cl. ..................................... 250/458.1; 250/565
(58) Field of Search ............................... 250/458.1, 565

(56) References Cited

U.S. PATENT DOCUMENTS

| 4,234,540 A | 11/1980 | Ginsberg et al. |
| 4,285,906 A | 8/1981 | Meltzer et al. |
| 4,844,887 A | * 7/1989 | Galle et al. .................. 422/65 |

FOREIGN PATENT DOCUMENTS

| DE | 195 22 919 A1 | 1/1997 |
| EP | 0 457 526 A2 | 11/1991 |
| FR | 2 622 305 A | 4/1989 |
| WO | WO 83 03900 A | 11/1983 |

* cited by examiner

Primary Examiner—Constantine Hannaher
Assistant Examiner—Otilia Gabor
(74) Attorney, Agent, or Firm—Sughrue Mion, PLLC

(57) ABSTRACT

An apparatus including a sample holder which fixedly holds sample vessels arranged on a same arc, a partition plate, a light guide which is configured by optical fibers and which transmits fluorescent signals emitted from respective test samples, to an optical sensor, the single optical sensor, and a light source which generates excitation light. Fluorescent signal emission ends of the light guide are opposed to the optical sensor, and fluorescent signal incidence ends of the light guide are respectively opposed to the sample vessels via the partition plate therebetween. The partition plate includes an excitation light optical unit for selectively guiding the excitation light from the light source to only one of the sample vessels arranged on the arc, and a fluorescence optical unit for guiding only the fluorescent signal emitted from a selected one of the sample vessels to the light guide. The partition plate is coupled together with the excitation light optical unit and the fluorescence optical unit to a driving unit, to be rotatable about a center of the arc on which the sample vessels are arranged. Fluorescence is detected while the excitation light is guided sequentially to the sample vessels arranged on the arc, by rotation of the partition plate.

5 Claims, 6 Drawing Sheets

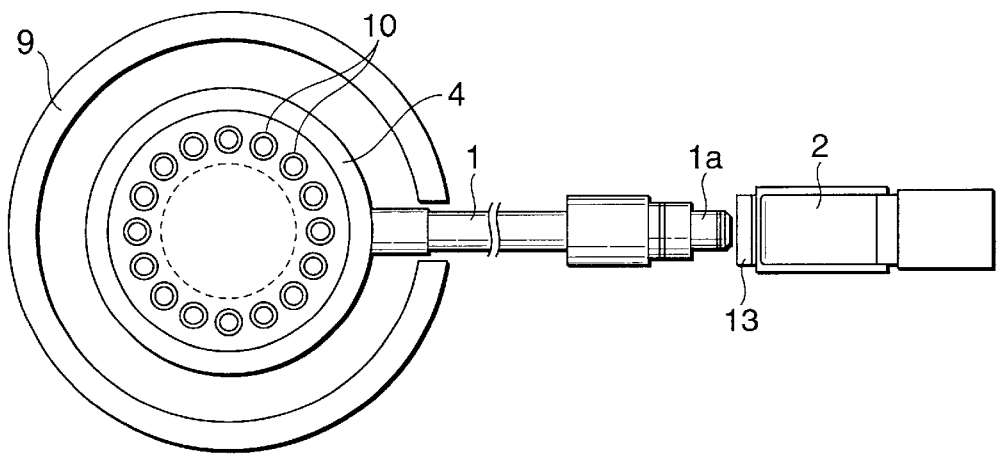
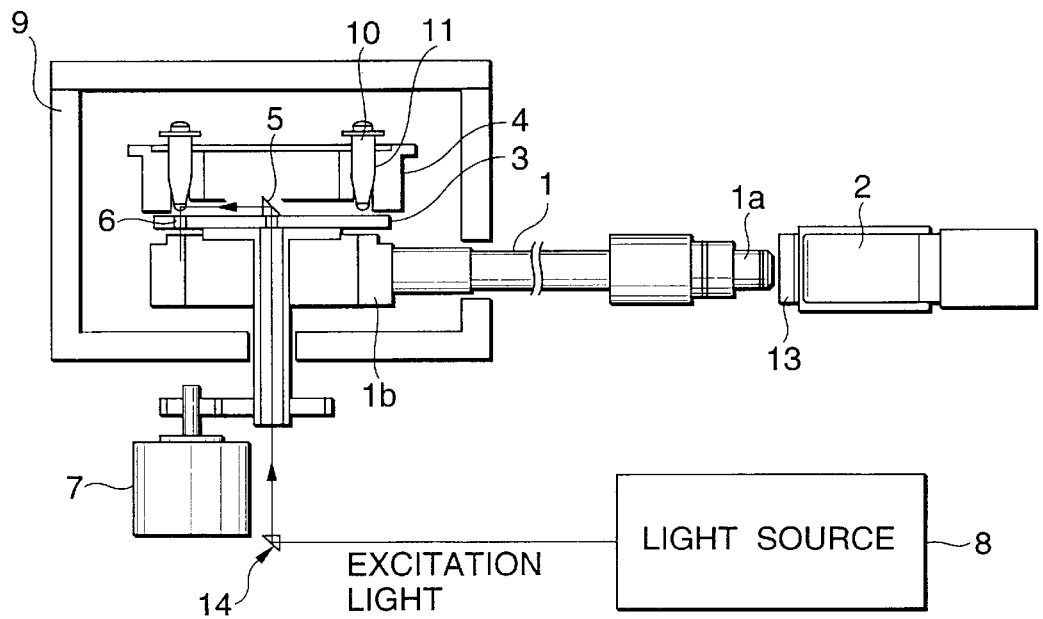

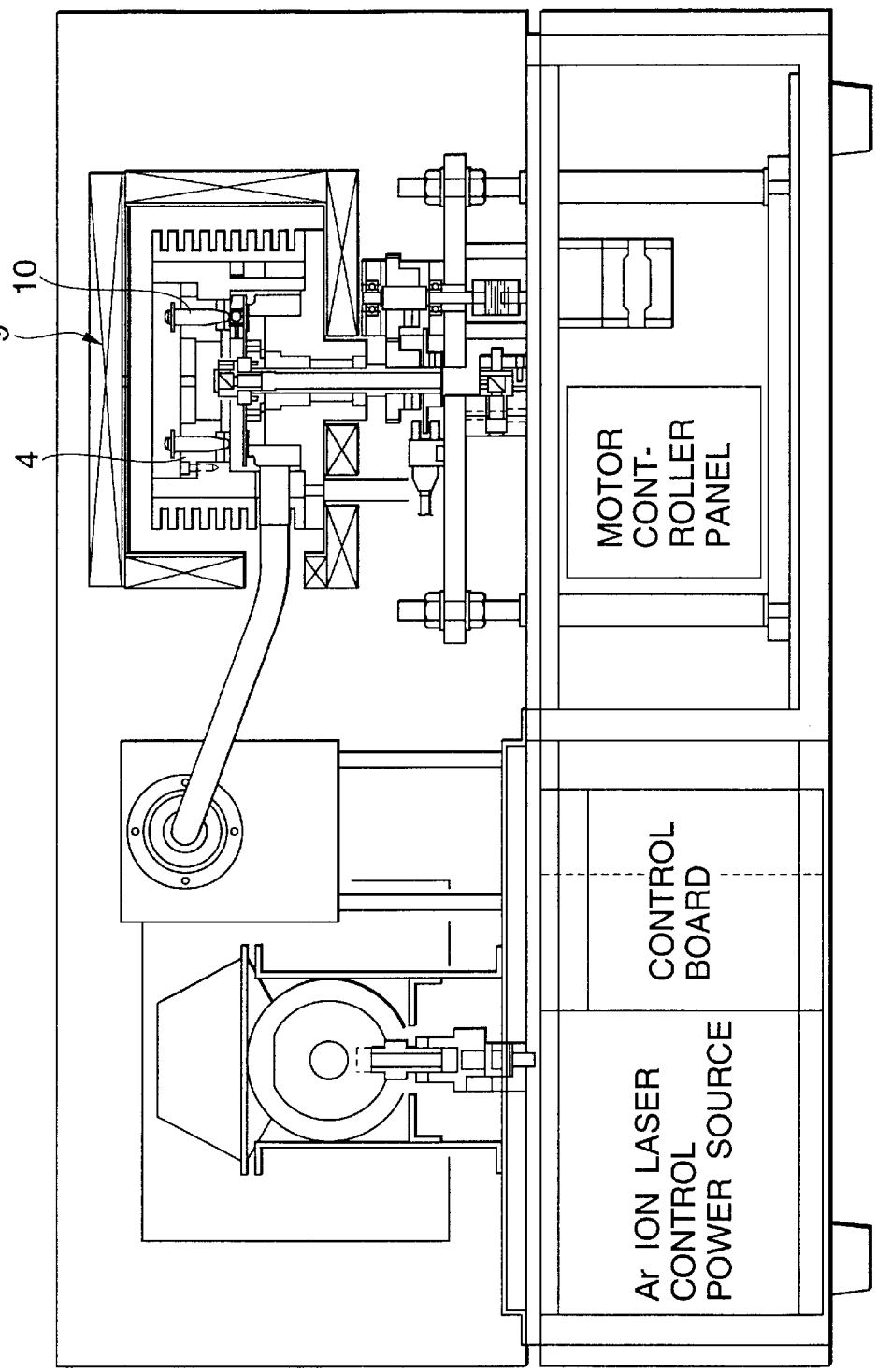

SCANNER TYPE FLUORESCENCE DETECTION APPARATUS

BACKGROUND OF THE INVENTION

1. Field of the Invention

The present invention relates to a fluorescence detection apparatus which detects a fluorescent signal emitted from a specific substance contained in a sample, and which determines the amount of the substance based on the amount of the detected fluorescent signal, and more particularly to a fluorescence detection apparatus which is useful in the case where real time monitoring (tracking of a temporal change in the amount of a fluorescent signal) of a large number of samples is performed in the field of clinical diagnosis requiring incubation at a predetermined temperature, such as an enzyme reaction.

2. Description of the Related Art

The manner of producing a fluorescent reaction product due to an enzyme reaction may be monitored in real time. In such a case, fluorescence detection must be performed while incubating a sample (reaction solution) at a predetermined temperature. In the field of clinical diagnosis and the like, moreover, a large number of samples must be promptly processed at the same time.

In a first one of methods which are conventionally used in the field of clinical diagnosis and the like, fluorescence detection is performed while samples are transported along a guide the temperature of which is adjusted. For example, the temperature of a guide which is made of a material of excellent thermal conductivity such as an aluminum alloy is adjusted by means of a heater or the like. One or plural samples placed on a holder are transported along the guide by using a chain, a turntable, or the like. Fluorescent signals are sequentially detected by a fluorescence detector which is placed along the guide.

Another method is known in which connection type sample vessels, titer plates, or the like that can house a large number of samples are placed on temperature adjusting means, so that fluorescence detection is simultaneously performed on the large number of samples. A fluorescence detection apparatus which is useful in this case is characterized in that the apparatus is provided with (a) plural optical sensors or (b) a multichannel optical sensor, or has mechanical moving means for moving an optical sensor or a light guide (means for guiding a fluorescent signal emitted from a sample vessel to an optical sensor, such as an optical fiber).

The apparatus of (a) is a fluorescence detection apparatus in which optical sensors the number of which corresponds to that of samples to be simultaneously subjected to fluorescence detection are used and fluorescent signals emitted from the samples are independently detected. Such an apparatus usually has a configuration wherein a light guide for splitting excitation light from a light source and then guiding the split excitation light to samples is used.

In the apparatus of (b), an image sensor such as a CCD or a photodiode array is used in place of the plural optical sensors of (a). According to this configuration, fluorescent signals emitted from the arranged samples are detected as an image under a state where positional relationships among luminescent points are maintained. Also in such an apparatus, a configuration is usually employed in which excitation light from a single light source is guided to samples by using a split type light guide (an optical device, an optical fiber, or the like).

In the apparatus of (c), the optical sensor is mechanically moved over a large number of samples or the samples are sequentially moved to a fluorescence detection position for the optical sensor. In such an apparatus, the configuration wherein a light guide is mechanically moved is used most commonly. In this configuration, an excitation light guide and a fluorescence light guide are used, ends of the guides which are on the side of the samples are integrated with each other, and the guides are then simultaneously moved, whereby fluorescence is detected while sequentially exciting the large number of samples.

When such a conventional fluorescence detection apparatus is used for monitoring in real time a temporal change in a fluorescent signal emitted from a specific substance contained in a sample while incubating the sample at a predetermined temperature, there arise the following problems.

In the first method, the samples are transported along the temperature-adjusted guide, and then sequentially subjected to fluorescence detection. Consequently, there are problems such as an insufficient accuracy of the temperature adjustment, a limited number of processable samples, and a possibility of carryover. Specifically, it is difficult to adjust the whole of the transport guide so as to have a uniform temperature, and the thermal conductivity between the transport guide and the samples is hardly maintained constant over the whole of the guide. As a result, the temperatures of the samples may be changed during transportation, or the samples may be different in temperature from one another. Furthermore, the transported samples are subjected to fluorescence detection one by one. When the temporal change in a fluorescent signal is to be monitored for a long period, the same sample must be repeatedly transported. Therefore, the number of processable samples has its limit. Moreover, the possibility of contamination (carryover) among the samples due to splashes of the samples cannot be eliminated.

In the second method, the problems of the first method can be solved, but the following further problems may be produced.

In (a), plural optical sensors must be disposed. Therefore, the production cost is increased, and a space which corresponds to the number of the optical sensors is required. When the apparatus is to be miniaturized, the limitation on the space enables only several optical sensors to be disposed. As a result, the number of samples which can be simultaneously processed remains to be small. It may be contemplated that optical sensors of a small size such as photodiodes are used. However, such optical sensors have a drawback that the sensitivity to weak fluorescence is insufficient. Moreover, the sensitivity of each photodiode must be corrected. There is a further problem that the intensity of a fluorescent signal is proportional to that of the excitation light and hence splitting of the excitation light from the light source causes deterioration of the detection sensitivity.

In (b), sensitivity to weak fluorescence is insufficient. Therefore, (b) is not suitable for detection of weak fluorescence. In order to compensate the insufficient sensitivity, a measure such as a device (so-called image intensifier) which amplifies the amount of light by means of electronic amplification using a microchannel plate is sometimes further employed. In this case, however, the cost is very high. At present, therefore, such a measure is employed only in a special study purpose. Since fluorescence emitted from a wide area is detected as an image, there arise further problems that the amount of light is unevenly detected because of lens aberration, and that the burden of the data processing is increased by the extreme amount of data.

In (c), because of the limitation of the bendability of the light guide, the movement range is restricted, and there is a possibility that the light guide is broken. In the light guide, moreover, the light transmission efficiency is changed by bending, and hence fluorescence detection is hardly performed with high reproducibility. On the other hand, also the mechanical movement of the optical sensor involves the movement of a cable and other components, and hence has problems that the movement range is restricted, and that there is a possibility of breaking the cable or the like.

As described above, a fluorescence detection apparatus for monitoring a fluorescent signal in real time, and particularly that for performing monitoring in real time while incubating samples at a predetermined temperature must satisfy requirements such as (a) highly accurate temperature adjustment, (b) prompt treatment of a large number of samples, (c) high sensitivity, (d) high reliability (reduction in number of mechanical troubles typified by a cable breakage and malfunction of movable parts, improvement of reproducibility of fluorescence detection, and reduction of probability of carryover), (e) low cost (simplification of the configuration of the apparatus, and nonuse of expensive components in data processing and the like), and miniaturization of the apparatus.

SUMMARY OF THE INVENTION

Therefore, it is an object of the invention to provide a fluorescence detection apparatus which can satisfy the above requirements.

In order to attain the object, according to the invention, there is provided a fluorescence detection apparatus which detects a fluorescent signal emitted from a specific substance of a sample taken in a sample vessel, the apparatus comprising: a sample holder which fixedly holds sample vessels arranged on a same arc; a partition plate; a light guide which is configured by optical fibers and which transmits fluorescent signals emitted from respective test samples, to an optical sensor; the single optical sensor; and a light source which generates excitation light, wherein fluorescent signal emission ends of the light guide are opposed to the optical sensor, and fluorescent signal incidence ends of the light guide are respectively opposed to the sample vessels via the partition plate therebetween, wherein the partition plate includes excitation light optical means for selectively guiding the excitation light from the light source to only one of the sample vessels arranged on the arc, and fluorescence optical means for guiding only the fluorescent signal emitted from the selected one of the sample vessels to the light guide, and wherein the partition plate is coupled together with the excitation light optical means and the fluorescence optical means to driving means, to be rotatable about a center of the arc on which the sample vessels are arranged, and fluorescence is detected while the excitation light is guided sequentially to the sample vessels arranged on the arc, by rotation of the partition plate.

BRIEF DESCRIPTION OF THE DRAWINGS

FIG. 1A is a top view schematically showing a fluorescence detection apparatus of the invention.

FIG. 1B is a front view schematically showing the same.

FIG. 3B is a front view illustrating the same.

DETAILED DESCRIPTION OF THE PREFERRED EMBODIMENT

Figure 2A:
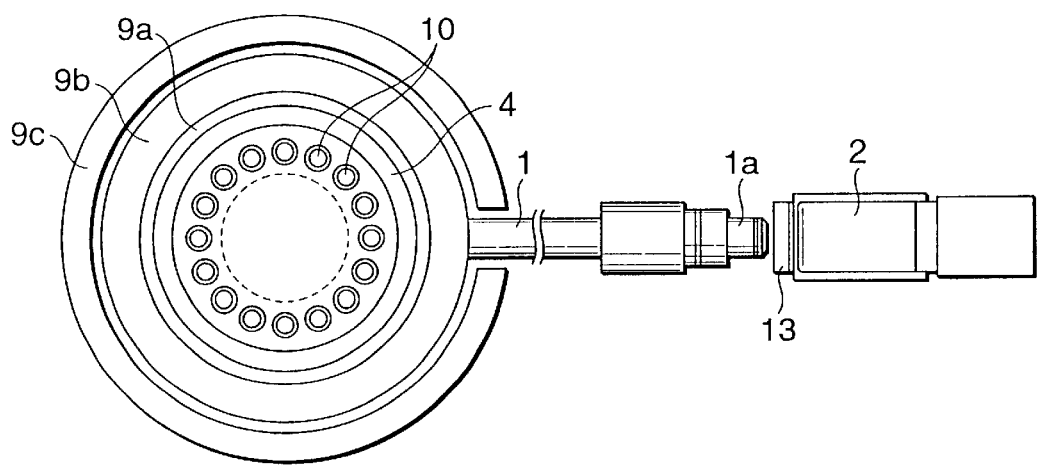
FIG. 2A is a top view schematically showing the fluorescence detection apparatus of the invention provided with temperature adjusting means.

Hereinafter, a fluorescence detection apparatus of the invention will be described in detail with reference to the accompanying drawings.

FIGS. 1A and 1B schematically show an embodiment of a fluorescence detection apparatus for monitoring a fluorescent signal in real time while incubating samples at a predetermined temperature.

A sample holder 4 fixedly holds sample vessels 10 which respectively take samples therein, in a state where the sample vessels 10 are arranged on the same arc, that is, all the sample vessels 10 exist at positions separated from an arbitrary point by the same distance. Therefore, the sample holder 4 has holding holes 11 which are arranged on the arc and which correspond to the outer shape of each sample vessel. The arrangement of the sample vessels 10 is not restricted to the illustrated one in which the vessels are arranged at even intervals, and the sample vessels 10 may be arranged at uneven intervals as far as the sample vessels 10 are arranged on the same arc. The number of sample vessels which can be fixedly held by the sample holder 4 is not restricted, and may be determined in accordance with the length of the arc, the outer diameter of each sample vessel, and the like. The shape of the sample holder 4 in a top view is not restricted to a circle, and may be a polygon such as a tetragon.

The kind of the sample vessels 10 is not particularly restricted as far as the vessels are made of a material which can transmit excitation light and fluorescence, and which is chemically stable with respect to a sample to be taken in. The sample vessels 10 may be adequately selected in consideration of, for example, the amount of the sample which is to be used in fluorescence detection. In the case where, in so-called PCR, NASBA, or the like, the manner of reaction is monitored while amplifying nucleic acid, sample vessels having a sealing plug are preferably used in order to prevent amplified nucleic acid from scattering.

A partition plate 3 is coupled to driving means 7 and disposed below the sample holder 4 which is fixedly disposed, so as to be rotatable about the center of the arc on which the sample vessels 10 are arranged. The partition plate 3 is preferably configured by a disk in order to uniformalize the turning moment. The size (radius) of the partition plate 3 is set to be larger than at least the distance between the arc center and the sample vessels 10, so that the fluorescence path from one of the sample vessels 10 to a light guide 1 is interrupted except when fluorescence optical means (which will be described later) exists. Alternatively, the partition plate 3 may be disposed above the sample vessels 10. In the alternative, it is difficult to make a sample close to the light guide unless a sample vessel is filled with the sample, and the sample vessels 10 must be provided with a measure such as a hollowed structure in order to couple the partition plate 3 with the driving means 7, and a further measure such as that for detachably attaching the partition plate 3 in order to attach sample vessels 10 to the sample holder 4. Therefore, it is preferable to dispose the partition plate 3 below the sample holder 4.

In the apparatus of the invention, an optical fiber is used as the light guide 1 for transmitting a fluorescent signal generated by the corresponding sample on which the excitation light is irradiated, to an optical sensor 2. This is employed in order to transmit the fluorescent signal to the single optical sensor with avoiding attenuation of the signal. Preferably, plural bundled optical fibers are used as a light guide 1 so as to ensure a sufficient capacity.

Figure 4:
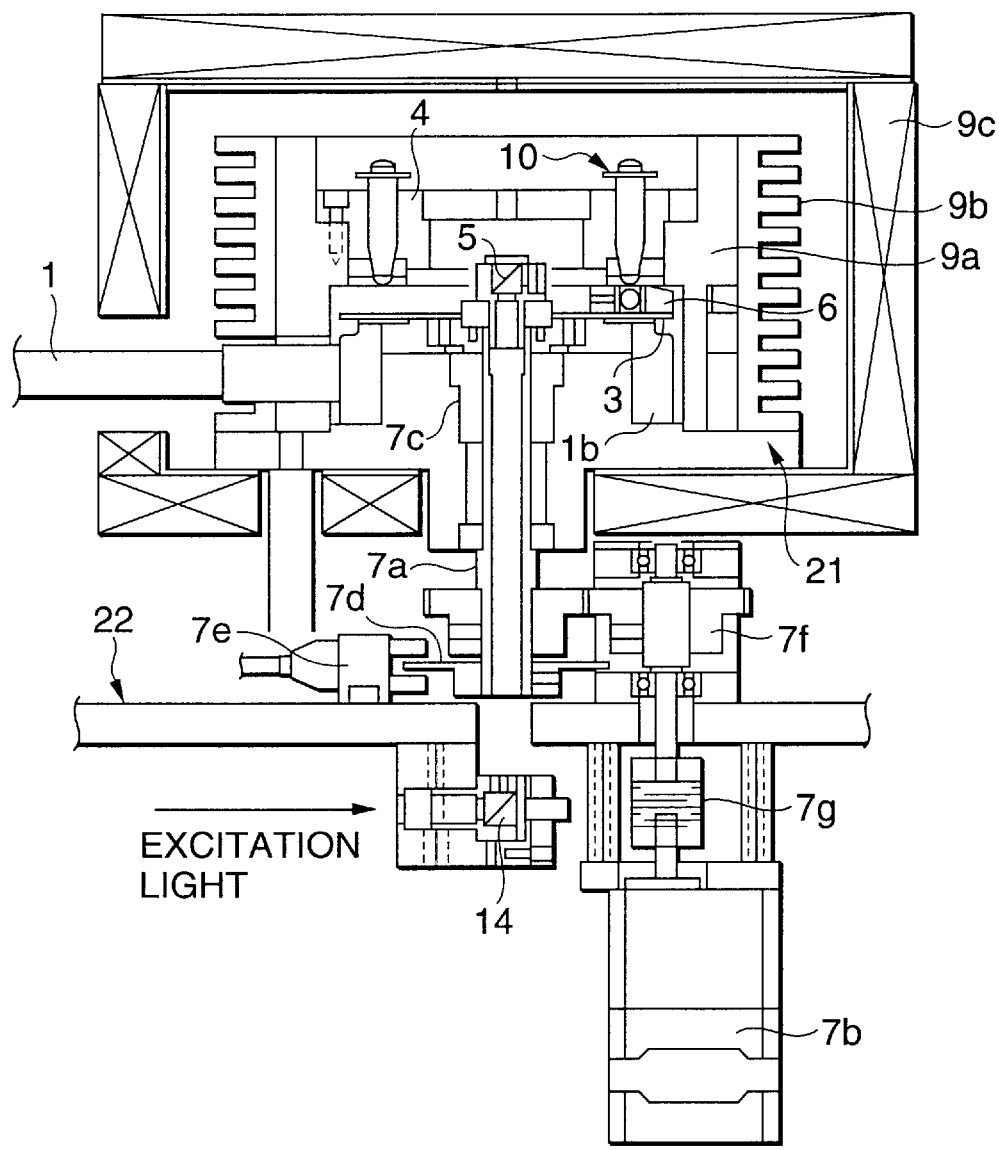
FIG. 4 is a front view illustrating in detail a part of the fluorescence detection apparatus shown in FIG. 3B.

Fluorescent signal emission ends of the light guides are opposed to the single optical sensor 2. Preferably, the ends and optical sensor are fixed with making them sufficiently close so that a fluorescent signal emitted from the end of each optical fiber enters the optical sensor 2 without being attenuated. It is particularly preferable to compactly bundle the ends of optical fibers by using a suitable fitting with aligning the end faces. Although the sensitivity of the light receiving surface of the optical sensor 2 is not necessarily uniform, this reduced end face area as a result of bundling the ends enables the fluorescent signal to be received by a portion where the sensitivity is relatively uniform. Fluorescent signal incidence ends 1b of the light guide 1 are fixedly arranged so as to be respectively opposed to the sample vessels 10 via the partition plate 3 therebetween. In place of the configuration wherein fluorescent signal incidence ends of optical fibers are arranged at intervals, a configuration may be employed wherein, as shown in FIG. 4, a ring light guide 12 in which plural light guides are integrated with one another and their fluorescent signal incidence ends are annularly arranged is used so that fluorescent signal incidence ends are arranged without forming gaps.

Although the apparatus of the invention performs fluorescence detection on a large number of samples, only one optical sensor 2 is disposed in the apparatus. The bundle 1a of fluorescent signal emission ends of the light guides 1 is fixedly disposed in the vicinity of the optical sensor 2. An optical filter 13 which selectively extracts a fluorescence wavelength to be detected is disposed between the bundle and the optical sensor. The optical filter 13 may be disposed between the light guides 1 and the optical sensor 2, and may be disposed in front of the fluorescent signal incidence ends 1b of the light guides 1, or as a part of the fluorescence optical means 6 disposed in the partition plate 3.

The partition plate 3 is provided with excitation light optical means and fluorescence optical means. The excitation light optical means is means for selectively guiding excitation light generated by a light source 8 to only one of the sample vessels 10 which are arranged on the arc. In the example of FIG. 1B, the means is configured by a reflecting mirror 5 which perpendicularly bends an optical path for the excitation light. The optical path is guided from the light source 8 via another reflecting mirror 14 to a hollow portion of a rotation shaft of the partition plate 3. The phrase of guiding excitation light to only one of the sample vessels 10 is not used in its strict meaning, and means that it is sufficient for excitation light to be intentionally guided to one of the sample vessels 10. Even if a small amount of excitation light is caused to reach another sample vessel by reflection from the outer wall of the one sample vessel, for example, there arises no particular problem. In the case where a small excitation light source such as a semiconductor laser (laser diode) or a light emitting diode is used, the light source itself may be fixed onto the rotating partition plate unlike the example of FIGS. 1A and 1B. According to this configuration, the excitation light optical means 5 may be omitted.

The light source 8 may be adequately selected in consideration of the excitation wavelengths of the samples so that a sufficient amount of excitation light reaches each sample vessel via the excitation light optical means 5. In order to guide the excitation light to only one sample vessel, preferably, the excitation light may be parallel rays, or converted into parallel rays by using conventional optical components. Specifically, useful light sources are exemplified by a laser light source such as an argon ion laser or a semiconductor laser (laser diode), and a light emitting diode.

The fluorescence optical means 6 which is disposed on the partition plate 3 is means for guiding only the fluorescent signal emitted from the one sample vessel to which the excitation light is guided as described above, to the light guide 1 opposed to the sample vessel. As described above, even if fluorescence is emitted from other sample vessels, the partition plate 3 prevents the fluorescence from reaching the light guide, thereby controlling fluorescence so as not to simultaneously enter the optical sensor 2. According to this configuration, the provision of the single optical sensor 2 enables fluorescent signals of all the large number of samples to be intermittently monitored in real time.

The fluorescence optical means 6 may be configured by a small hole or a slit for transmission of fluorescence and formed in a portion through which a sample vessel 10 is connected to the fluorescent signal incidence end 1b of the light guide 1 opposed to the sample vessel. It is a matter of course that an optical component such as a condenser lens may be disposed in this portion.

In the apparatus of FIGS. 1A and 1B configured as described above, the sample vessels 10 fixedly held on the sample holder 4 are sequentially irradiated one by one with excitation light by the excitation light optical means 5 in accordance with the rotation of the partition plate 3. At the same time, fluorescence emitted from the sample vessels 10 enters the light guide 1 via the fluorescence optical means 6, and then detected by the optical sensor 2. While controlling the rotation of the partition plate 3 by using a computer or the like, detection results of the optical sensor 2 are accumulated. As a result, intermittent fluorescence detection results of an arbitrary one of the samples held on the sample holder 4 can be obtained, and hence real time monitoring can be realized.

Figure 2B:
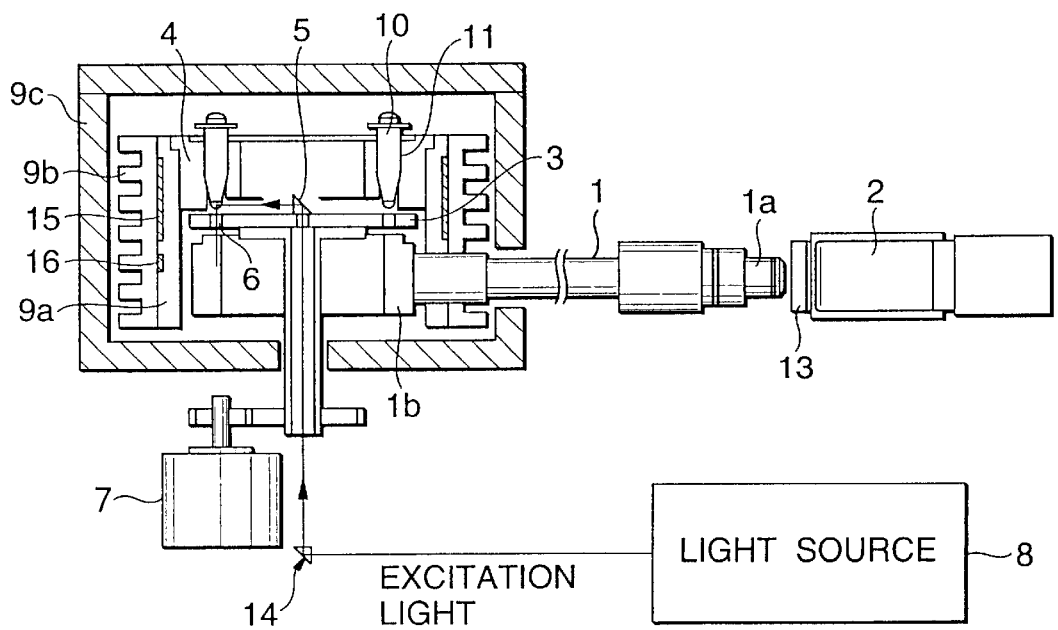
FIG. 2B is a front view schematically showing the same.
Figure 3A:
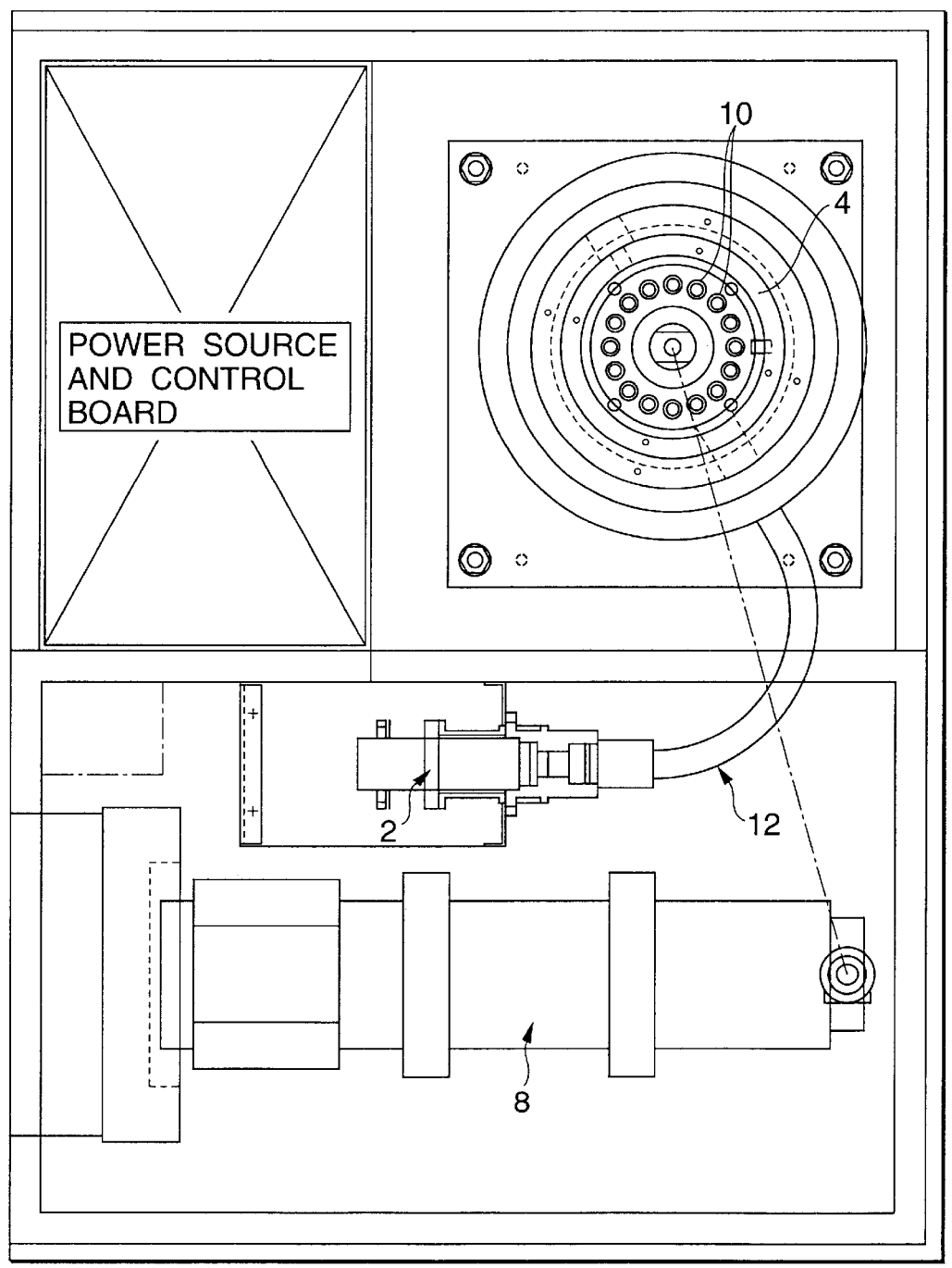
FIG. 3A is a top view illustrating an embodiment of a fluorescence detection apparatus in the invention.

FIGS. 2A and 2B are views schematically showing temperature adjusting means for allowing the real time monitoring to be performed while incubating a sample at a predetermined temperature. The temperature adjusting means is configured by: a temperature adjusting block 9a including a heater 15 and a control temperature sensor 16; a fin-like block 9b connected to an outer periphery of the temperature adjusting block; and a heat insulating case 9c which houses the temperature adjusting block and the fin-like block, via an air layer. The sample holder 4 holding sample vessels 10 is housed in the temperature adjusting block 9a. The temperatures of the samples are accurately adjusted by heat conduction from the temperature adjusting block 9a and natural convection of the air layer which is heated by the fin-like block 9b. In a case such as that where it is requested only to roughly adjust the temperature of a sample, a simple configuration may be employed. For example, a heater is disposed in the heat insulating case 9c, or the sample holder is made of a material of excellent thermal conductivity, and means for adjusting the temperature of the holder itself is disposed. In the example of FIGS. 2A and 2B, heating means based on a heater is used as the temperature adjusting means. Alternatively, the temperature may be set to be lower than ordinary temperatures by cooling means such as a Peltier element. When both heating means and cooling means are disposed, the apparatus can cope with incubation in which heating and cooling are repeated, such as PCR (Polymerase Chain Reaction).

Hereinafter, in order to describe the fluorescence detection apparatus of the invention in more detail, a specific example will be described with reference to FIGS. 3A to 5B. The invention is not restricted to the example.

FIGS. 3A to 5B are views illustrating the fluorescence detection apparatus of the invention in detail.

As a light guide 1 in which a large number of optical fibers are bundled, used is a ring light guide (diameter of a fiber strand: φ30 μm, number of fiber strands: about 90,000, diameter of a bundle: φ9.5 mm, and diameter of a ring: φ67 mm) which is often used as illumination transmitting means for an optical microscope. Such a ring light guide is originally used for the purpose of receiving illumination light through a bundle portion and irradiating an observation object of an optical microscope with light emitted from a ring portion. In this example, the light transmission direction of the ring light guide is inverted, or the ring portion is used as an incidence end for fluorescent signals, and the bundle portion as an emission end. In the ring light guide, optical fibers are arranged in a ring-like (arcuate) manner without forming gaps. In order to attain the object of the invention, optical fibers may be intermittently arranged so as to respectively correspond to sample vessels 10. From the view point of efficiently collecting fluorescent signals, such an intermittent arrangement may be more preferable.

An optical sensor (photomultiplier) 2 is disposed in the vicinity of the fluorescent signal emission end (bundle portion) 1a of the ring light guide 1, via an optical filter 13 (520 nm) for wavelength selection. A sample holder 4 is disposed in the vicinity of the fluorescent signal incidence end (ring portion) 1b, via a partition plate 3.

Figure 5A:
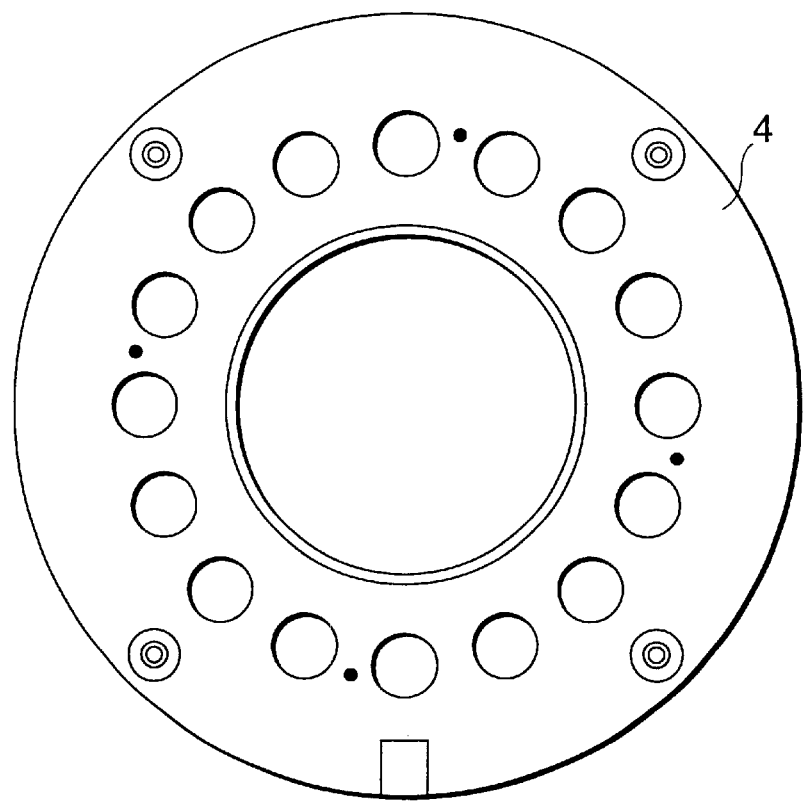
FIG. 5A is a top view illustrating in detail a part of the sample holder of the fluorescence detection apparatus shown in FIGS. 3A and 3B.
Figure 5B:
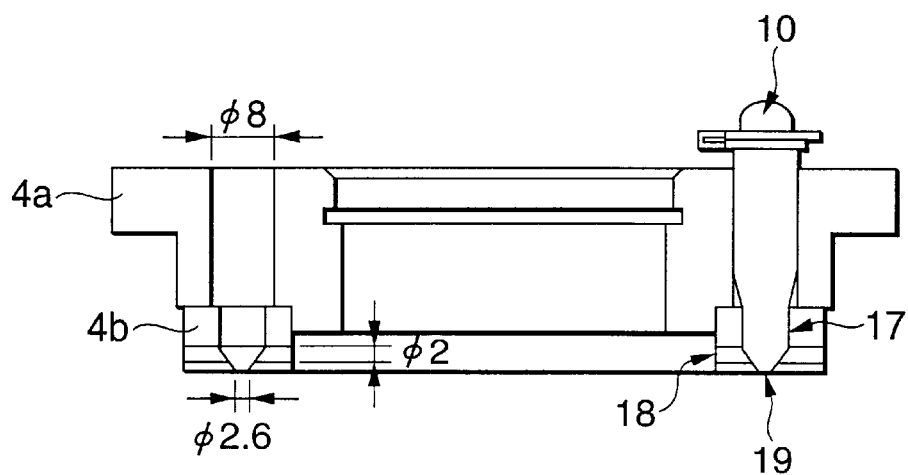
FIG. 5B is a sectional front view illustrating in detail the same.

As shown in FIGS. 4 and 5B, the sample holder 4 is configured by vertically combining two annular aluminum alloy parts with each other. In the upper annular part 4a, in order to insertingly hold 16 sample vessels 10, 16 holes 11 (φ8 mm) which are suitable to the outer diameter of a sample vessel are formed at even intervals on an arc which elongates along the ring portion 1b of the light guide 1. In the lower annular part 4b, 16 recesses 17 which support the bottoms of the sample vessels 10, 16 holes 18 (φ2 mm) through which excitation light is to pass, and 16 holes 19 (φ2.6 mm) through which fluorescent signals are to pass toward the light guide are formed at positions corresponding to the 16 holes 11 of the upper annular part 4a, respectively.

The disk-like partition plate 3 is placed between the fluorescent signal incidence end 1b of the light guide 1 and the sample holder 4. As excitation light optical means 5, a rectangular prism is fixed to a center portion of the partition plate 3, in order to perpendicularly reflect excitation light which enters along a rotation shaft from the lower side of a rotation shaft 7a, and direct the reflected excitation light to one of the sample vessels 10. As fluorescence optical means 6, one set of a hole through which a fluorescent signal is to pass, and a ball lens for collecting fluorescence is disposed in an outer peripheral portion of the partition plate 3, and at a position which, when the partition plate 3 is rotated, crosses a line between a fluorescence generating point of a sample in each sample vessel and the fluorescent signal incidence end face of the light guide. In the excitation light optical means 5 and the fluorescence optical means 6, the direction of the prism and the positions of the holes are adjusted so that excitation light is guided to one sample vessel and only a fluorescent signal emitted from the one sample vessel is passed.

Driving means 7 is coupled to the partition plate 3. The driving means 7 is configured by the cylindrical rotation shaft 7a, a stepping motor 7b, a bearing 7c, a rotary slit 7d, a rotation position sensor 7e, a transmission gear 7f, and a coupling 7g. According to this configuration, the partition plate 3, and the excitation optical means 5 and the fluorescence optical means 6 fixed to the plate 3 are rotated as a unit in accordance with the operation of the driving means 7. The rotary slit 7d and the rotation position sensor 7e are disposed so as to enable detection of the state of the rotation of the partition plate 3, i.e., the position of the sample vessel which undergoes the fluorescence detection at each moment.

Among the components described above, all the components except the sample holder 4 are designed and assembled together so that their positional relationships are defined by base plates 21 and 22, and columns. As a reflecting mirror which allows the excitation light emitted from the excitation light source 8 to propagate along the rotation shaft, a rectangular prism 14 is disposed on the base plate 22 so as to be finely adjustable.

As the excitation light source 8, an argon ion laser is used so that laser light of 488 nm incidents on the rectangular prism 14 disposed on the base plate 22.

Temperature adjusting means is configured by: a temperature adjusting block 9a including a heater 15 and a control temperature sensor 16; a fin-like block 9b connected to an outer periphery of the temperature adjusting block; and a heat insulating case 9c which houses the temperature adjusting block 9a and the fin-like block 9b, via an air layer. The temperature adjusting block 9a and the fin-like block 9b are made of an aluminum alloy of excellent thermal conductivity. As the heater 15, a tape heater is wound around the outer periphery of the temperature adjusting block 9a. As the control temperature sensor 16, a platinum resistance thermometric element is bonded to the outer periphery. The heat insulating case 9c is configured by winding foamed polyethylene of a thickness of 14 mm around the outer side of a steel case of a thickness of 2 mm.

Among the components described above, the ring portion 1b of the light guide 1, the sample holder 4, the partition plate 3, and the excitation light optical means 5 and the fluorescence optical means 6 which are disposed on the partition plate 3 are housed inside a thermostatic bath 9. The bundle portion 1a of the light guide 1, the optical sensor 2, the excitation light source (argon ion laser 8), and the most of the driving means 7 for the partition plate are disposed outside the thermostatic bath 9. Since the sample holder 4 is housed in the temperature adjusting block 9a as described above, the temperatures of the samples can be accurately adjusted by means of heat conduction from the temperature adjusting block 9a and natural convection of the air layer which is heated by the fin-like block 9b.

The fluorescence detection apparatus described above operates in the following manner to detect a fluorescent signal of a sample. Laser light emitted from the argon ion laser 8 is reflected by the reflection prism 14 disposed below the rotation shaft 7a, in the upward direction or along the rotation shaft. The laser light is then reflected by the rectangular prism 5 disposed on the partition plate 3, toward one of the sample vessels, and excites the sample housed in the sample vessel 10. Fluorescence generated by the sample is emitted through a lower portion of the sample holder 4, passed through the hole and the fluorescence collecting ball lens of the fluorescence optical means 6 disposed in the partition plate 3, and then collected in the fluorescent signal incidence end (ring portion) 1b of the light guide 1. The fluorescence transmitted through the light guide is subjected to wavelength selection by the interference filter 13 of 520 nm, converted into an electric signal by the photomultiplier 2, and then detected.

The 16 sample vessels 10 are fixedly arranged on the arc at even intervals. In accordance with the rotation of the partition plate 3, therefore, excitation by laser light and collection of fluorescence by the fluorescence optical means 6 are sequentially executed on the samples. This means that fluorescence detection can be easily realized for a large number of samples (in this example, 16 samples). When the partition plate 3 is repeatedly rotated for a long period, the manner of the temporal change of fluorescent signals of the samples can be intermittently monitored in real time.

The fluorescence detection apparatus of the invention can attain the following effects.

Since the sample holder which can hold plural sample vessels is fixedly disposed, the temperatures of samples taken in the sample vessels can be accurately adjusted. Therefore, a large number of samples can be promptly processed. When the temperature adjusting means configured by a thermostatic bath based on a combination of heat conduction and natural convection is additionally disposed, particularly, temperature adjustment which is extremely accurate can be performed. Since the sample vessels are fixed and are not transported, possibilities that temperatures of samples are varied during transportation, and that carryover is caused by vibration or a shock during transportation can be eliminated.

Even in the case where the temperature adjusting means is disposed, the optical sensor can be disposed in the outer side with respect to the means. Therefore, increase of noises due to a temperature rise does not occur and hence highly sensitive signal detection is enabled. Since only one optical sensor is used, the production cost can be reduced, and the apparatus can be miniaturized. When plural optical sensors are used, a cumbersome work of correcting the sensitivities of the sensors is necessary. The use of only one optical sensor eliminates such a cumbersome work. In order to obtain the temporal change of fluorescent signals of many samples, moreover, it is requested only to process a signal from one optical sensor. Therefore, only a small burden is imposed on data processing. When a photomultiplier is used as the optical sensor, it is possible to provide a fluorescence detection apparatus of very high sensitivity. According to this configuration, sufficient sensitivity is ensured even for a weak fluorescent signal.

In the invention, also the optical fibers serving as the light guides are fixedly disposed. Therefore, the bending state of the optical fiber is never changed. Consequently, the light transmission efficiency is not changed by a change of the bending state of the optical fibers, with the result that signal detection can be performed with high reproducibility.

In the apparatus of the invention, mechanical moving parts are restricted to the partition plate and the optical means. Since these components are not accompanied by cables or the like, the movement range is not restricted, and there is no possibility that a cable is broken. Therefore, mechanical troubles can be suppressed to a minimum level. As described above, in the invention, although transportation of sample vessels or movement of the light guides is never performed, real time monitoring is realized by rotating the partition plate and the optical means.

As described above, the invention can provide a fluorescence detection apparatus which can perform real time monitoring while incubating samples at a predetermined temperature, and which satisfies requirements such as (a) highly accurate temperature adjustment, (b) prompt process of a large number of samples, (c) high sensitivity, (d) high reliability (reduction in number of mechanical troubles typified by a cable breakage and malfunction of a movable part, improvement of reproducibility of fluorescence detection, and reduction of probability of carryover), (e) low cost (simplification of the configuration of the apparatus, and nonuse of expensive components in data processing and the like), and miniaturization of the apparatus.

What is claimed is:

1. A fluorescence detection apparatus which detects a fluorescent signal emitted from a specific substance of a sample taken in a sample vessel, said apparatus comprising:

a sample holder which fixedly holds sample vessels arranged on a same arc;

a partition plate;

a light guide which is configured by optical fibers and which transmits flourescent signals emitted from respective test samples, to a single optical sensor;

said single optical sensor; and a light source which generates excitation light, wherein fluorescent signal emission ends of said light guide are opposed to said single optical sensor, and fluorescent signal incidence ends of said light guide are respectively opposed to said sample vessels via said partition plate therebetween, wherein said partition plate includes excitation light optical means for selectively guiding the excitation light from said light source to only one of said sample vessels arranged on the arc, and fluorescence optical means for guiding only the fluorescent signal emitted from the selected one of said sample vessels to said light guide, and wherein said partition plate is coupled together with said excitation light optical means and said fluorescence optical means to driving means, to be rotatable about a center of the arc on which said sample vessels are arranged, and fluorescence is detected while the excitation light is guided sequentially to said sample vessels arranged on the arc, by rotation of said partition plate.

2. The fluorescence detection apparatus according to claim 1, wherein said excitation light optical means includes a rectangular prism which perpendicularly reflects the excitation light from said light source to the one of said sample vessels.

3. The fluorescence detection apparatus according to claim 1, wherein said fluorescence optical means includes a set of a hole through which the fluorescent signal emitted from the one of said sample vessels is to pass, and a ball lens for collecting fluorescence.

4. The fluorescence detection apparatus according to claim 1, further comprising temperature adjusting means for housing at least said sample holder, and for controlling the samples to a predetermined temperature.

5. The fluorescence detection apparatus according to claim 4, wherein said temperature adjusting means includes a temperature adjusting block including a heater and a control temperature sensor, a fin-like block connected to an outer periphery of said temperature adjusting block, and a heat insulating case which houses said temperature adjusting block and said fin-like block via an air layer, and wherein said sample holder is housed in said temperature adjusting block, and the test samples in said sample vessels are adjusted to the predetermined temperature by heat conduction from said temperature adjusting block and natural convection of the air layer which is heated by said fin-like block.

* * * * *